United States Patent
Thornton et al.

(10) Patent No.: US 7,048,171 B2
(45) Date of Patent: May 23, 2006

(54) SURGICAL STAPLER WITH REMOVABLE STAPLE CARTRIDGE

(75) Inventors: Curtis W. Thornton, Raleigh, NC (US); Alberto Diaz, Apex, NC (US)

(73) Assignee: Dale H. Kosted, Enid, OK (US)

( * ) Notice: Subject to any disclaimer, the term of this patent is extended or adjusted under 35 U.S.C. 154(b) by 420 days.

(21) Appl. No.: 10/649,000

(22) Filed: Aug. 27, 2003

(65) Prior Publication Data

US 2005/0116008 A1   Jun. 2, 2005

Related U.S. Application Data

(60) Provisional application No. 60/406,574, filed on Aug. 29, 2002.

(51) Int. Cl.
*A61B 17/04* (2006.01)
*B31B 1/00* (2006.01)

(52) U.S. Cl. .................. 227/176.1; 227/19

(58) Field of Classification Search ........... 227/176.1, 227/19, 108, 112, 132, 134

See application file for complete search history.

(56) References Cited

U.S. PATENT DOCUMENTS

| | | | | | |
|---|---|---|---|---|---|
| 4,109,844 | A | * | 8/1978 | Becht | 227/120 |
| 4,179,057 | A | * | 12/1979 | Becht et al. | 227/19 |
| 4,375,866 | A | * | 3/1983 | Giersch et al. | 227/19 |
| 4,391,402 | A | * | 7/1983 | Campbell et al. | 227/121 |
| 4,591,086 | A | * | 5/1986 | Campbell et al. | 227/19 |
| 4,662,555 | A | * | 5/1987 | Thornton | 227/19 |
| 4,796,793 | A | * | 1/1989 | Smith et al. | 227/19 |
| 4,951,860 | A | * | 8/1990 | Peters et al. | 227/177.1 |
| 5,170,926 | A | * | 12/1992 | Ruckdeschel et al. | 227/177.1 |
| D332,491 | S | * | 1/1993 | Kraus et al. | D24/145 |
| 5,937,951 | A | * | 8/1999 | Izuchukwu et al. | 227/176.1 |
| 6,601,748 | B1 | * | 8/2003 | Fung et al. | 227/176.1 |

* cited by examiner

*Primary Examiner*—Scott A. Smith
*Assistant Examiner*—Brian Nash

(57) ABSTRACT

A surgical stapler which has an actuating trigger that is operable in three distinct positions. The actuating trigger works in combination with a forming tool and a window opening in a disposable staple cartridge to lock and align the centerline of a staple ready to be formed guaranteeing a smooth and precise insertion into a wound or incision.

2 Claims, 13 Drawing Sheets

SURGICAL STAPLER WITH REMOVABLE STAPLE CARTRIDGE

CROSS REFERENCE TO RELATED APPLICATIONS

"This application is entitled to the benefit of Provisional Patent Application Ser. No. 60/406,574, filed Aug. 29, 2002."

FIELD OF THE INVENTION

This invention relates to a surgical stapler for implanting staples into the skin and/or tissue for wound closure after a traumatic injury or a purposeful incision in a surgical procedure.

BACKGROUND OF THE INVENTION

It has become a preferred procedure to use staples for wound closure rather than thread or filament sutures. Surgeons choose staples because of the speed with which an incision can be closed as compared with the time consuming placing and tying of thread or filament sutures. Many surgical staplers have been designed with various features. See, for example, U.S. Pat. Nos. 8,601,748, 4,014,492, 4,109,844, 4,179,057, 4,202,480, 4,258,251, 4,375, 866, 4,407,286, 4,489,875, 4,527,725, and 4,682,555. The above patents describe staplers using preformed staples without a forming anvil, staplers having a stationary forming anvil, and staplers having a movable or retractable forming anvil as well as a wide variety of feeding mechanisms to deliver each staple to the delivery point where the staple is formed during implantation into the skin and/or tissue.

Although the use of surgical staplers are wide spread, still in most cost sensitive markets, such as veterinary surgery, thread or filament sutures are still most commonly used. In an effort to decrease the cost of using surgical staplers and allow staplers to be more cost efficient, one approach is to reduce the disposable portion of the stapler into a separate cartridge assembly to be used in conjunction with a reusable handle assembly. This decoupling of the cartridge and handle assemblies in turn creates other challenges related to the retention and alignment of the cartridge inside the handle. The present invention provides a novel structure to prevent this problem as explained more fully hereinafter.

BRIEF SUMMARY OF THE INVENTION

The surgical stapler with a removable staple cartridge of the present invention is formed of a combination of a handle assembly and a removable staple cartridge assembly, which are adapted to fit together so that an empty cartridge may be removed and replaced with a cartridge full of surgical staples. A partial closing of the handle assembly engages the forming tool into a beveled opening in the front of the removable staple cartridge locking the cartridge in the correct position in the handle so that a staple may be formed. The actuating trigger is then held in a latched position through a spring-loaded latch, which holds the handle assembly in a ready to use position but prevents the accidental disengagement of the removable staple cartridge assembly from the handle. The continued closing action of the handle assembly displaces the forming tool to form a staple into place. As the surgical staple which is fed between the form tool and the anvil portion of the removable staple cartridge rail as the leading one of a plurality of surgical staples pre-loaded into the removable staple cartridge assembly on a cartridge rail is moved toward and between the form tool and the anvil by the action of a clip pusher which is biased toward the form tool and anvil until inserted into the skin. The specific advantages of the present surgical stapler will be described and explained more fully in the following detailed description.

BRIEF DESCRIPTION OF THE DRAWINGS

The surgical staple applier of this invention will be described in more detail with reference to the accompanying drawings, which show one illustrative specific embodiment of the invention.

DETAILED DESCRIPTION OF THE DRAWINGS

Figure 1:
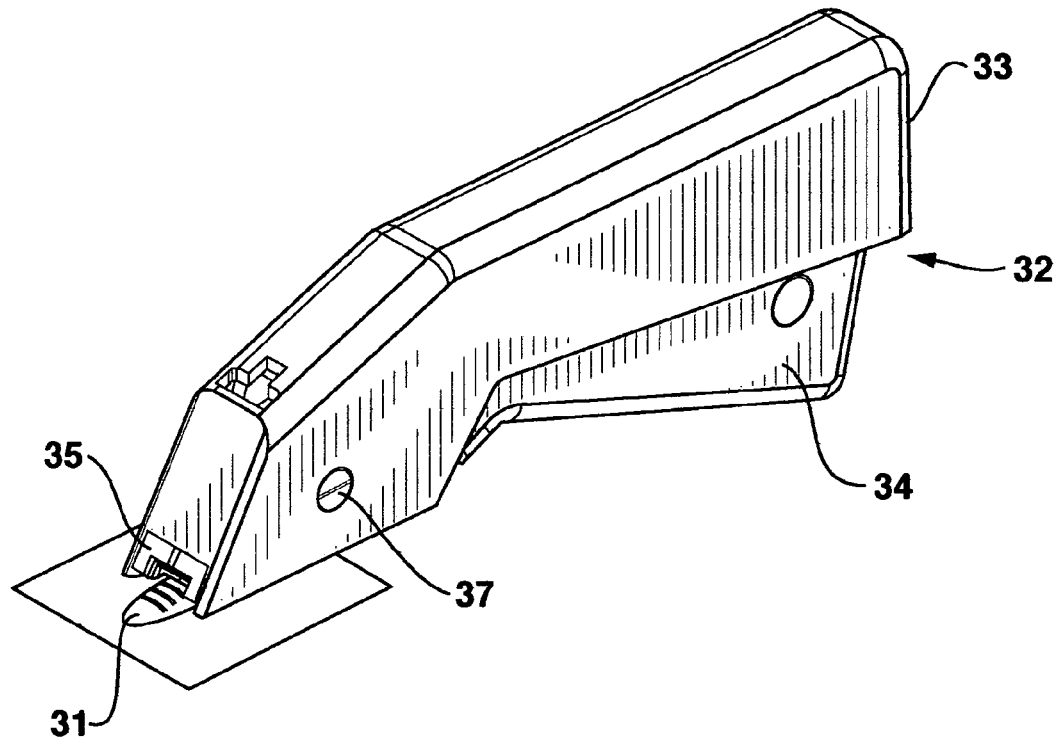
FIG. 1 is a perspective view of the surgical stapler handle assembly, with the removable staple cartridge loaded into the handle and the trigger in the latched position.

With reference to the accompanying drawings, the same parts are identified by the same reference numeral in all figures of the drawings.

In FIG. 1, a specific embodiment of the surgical stapler of the present invention, indicated generally by reference numeral 32, is shown in an attitude of use after having placed staples 38 to dose a wound for an incision 31. The surgical stapler 32 includes a handle assembly 33, an actuating trigger 34, and a removable staple cartridge 35 which are detachable from one another.

Figure 2:
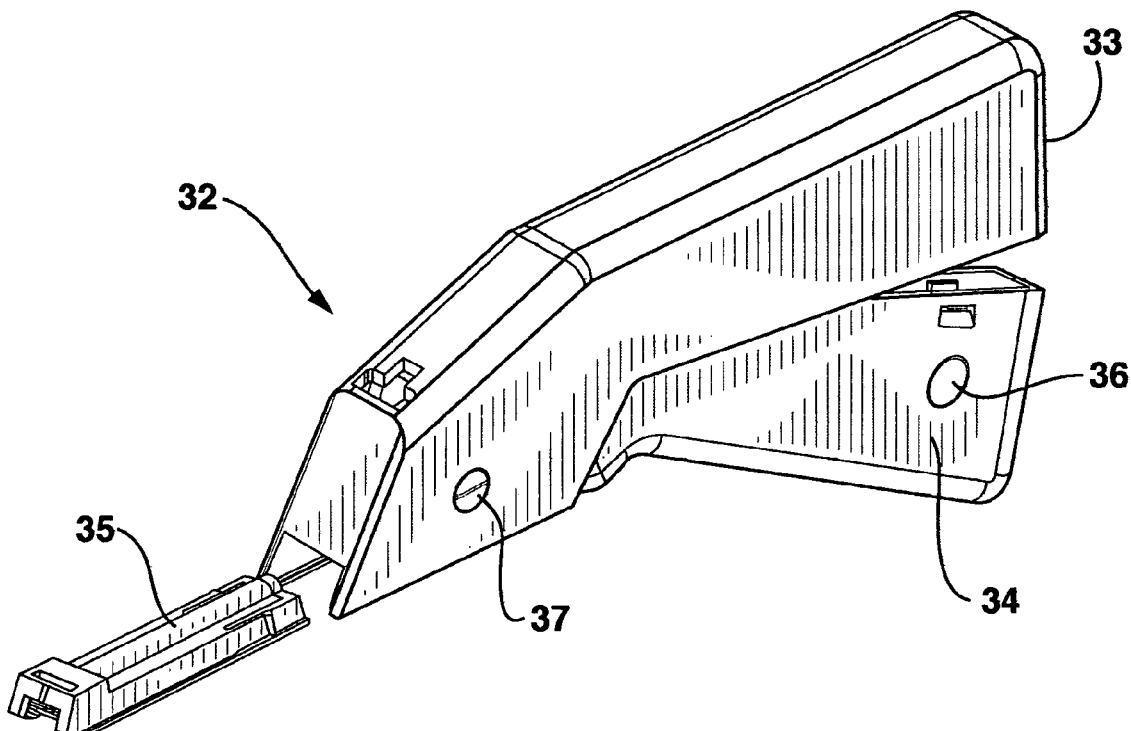
FIG. 2 is a perspective view of the surgical stapler assembly, with the actuating trigger in the open position and the removable staple cartridge removed.
Figure 3:
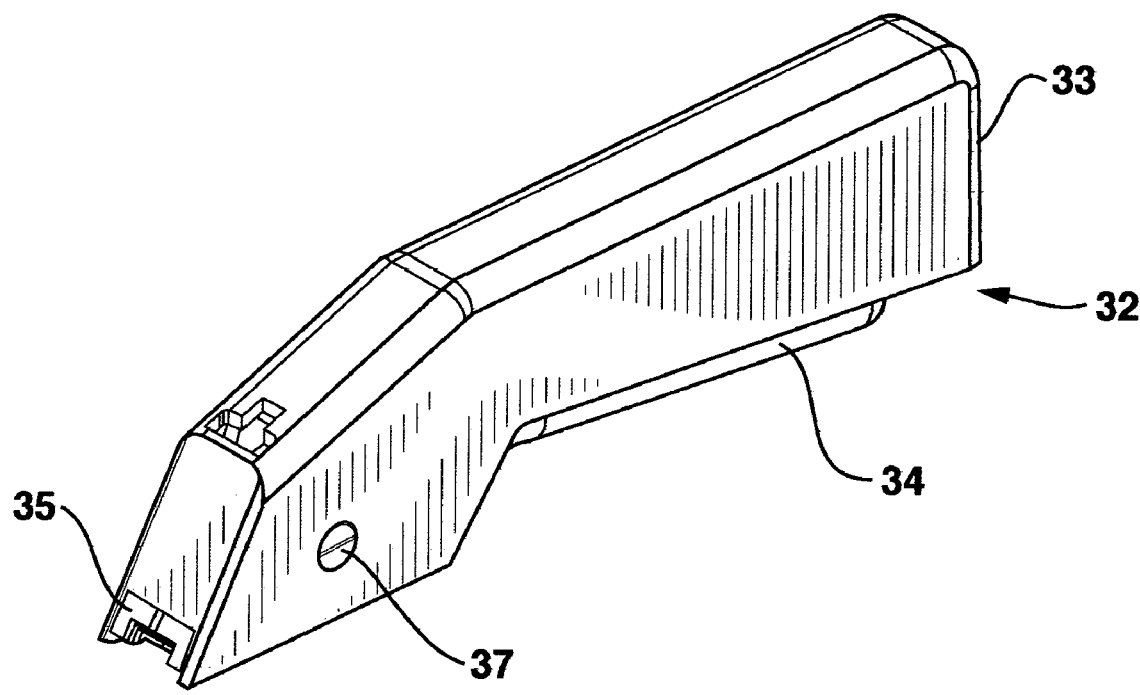
FIG. 3 is a perspective view of the surgical stapler assembly with the actuating trigger in the full closed position.
Figure 4:
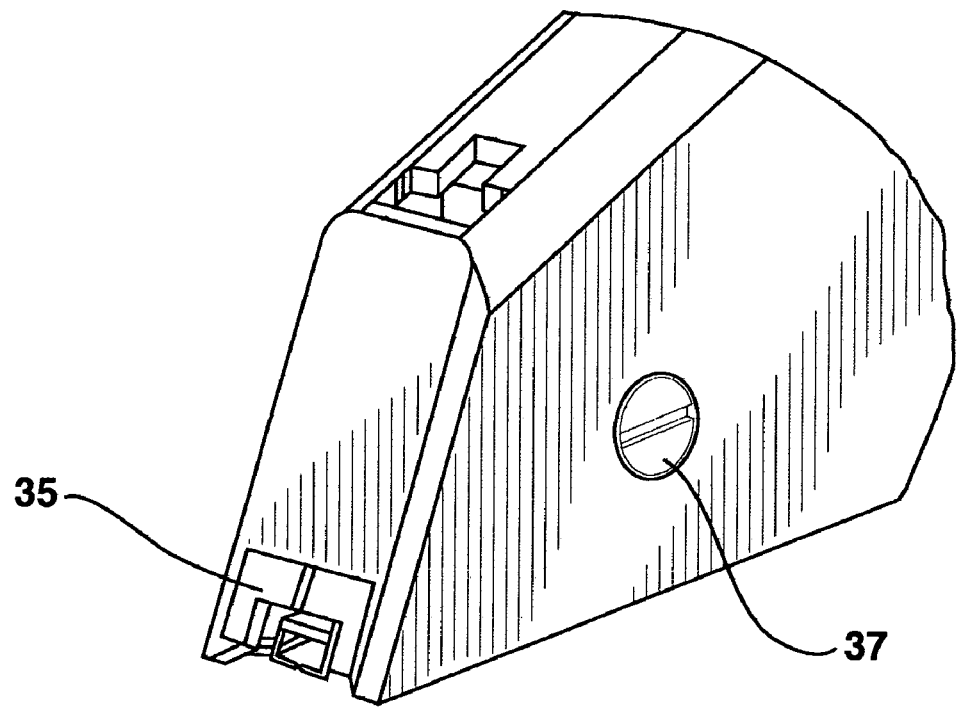
FIG. 4 is an enlarged partial view of the surgical stapler assembly in its full closed position and showing a staple completely formed.
Figure 5:
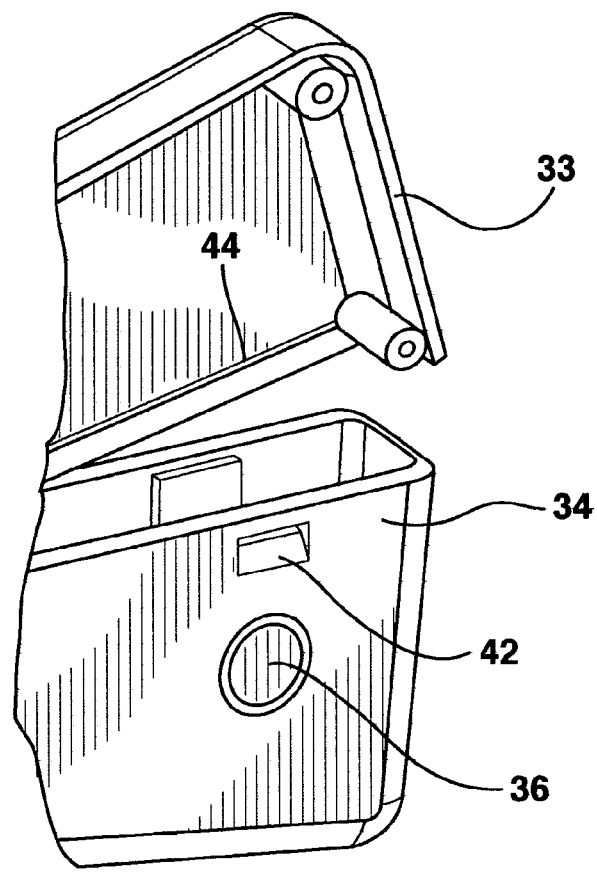
FIG. 5 is a detailed perspective view of the surgical stapler assembly in its fully open position with a partial view of the handle showing the actuating trigger release mechanism.
Figure 6:
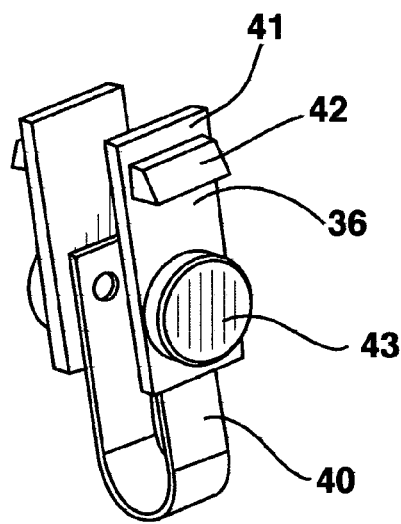
FIG. 6 is a perspective view of the actuating trigger release mechanism showing all its comprising components.
Figure 7:
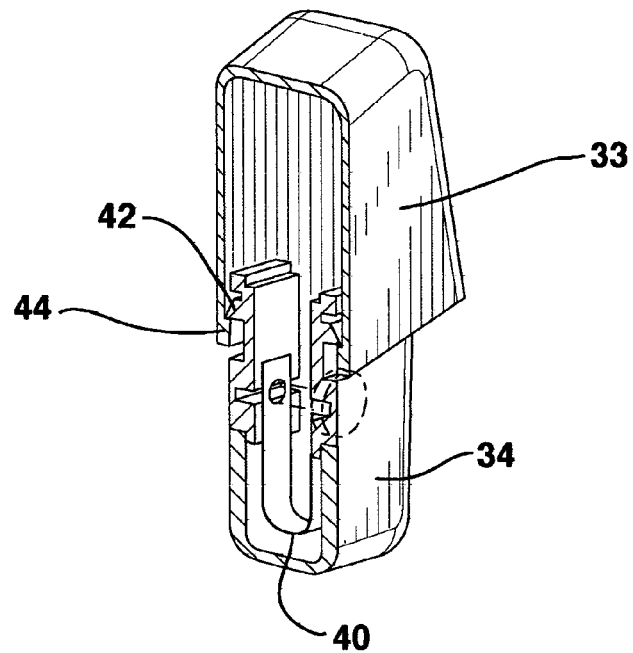
FIG. 7 is a section view of the latch assembly showing the position of the actuating trigger inside the handle assembly as the removable staple cartridge is locked in the applier handle.
Figure 8:
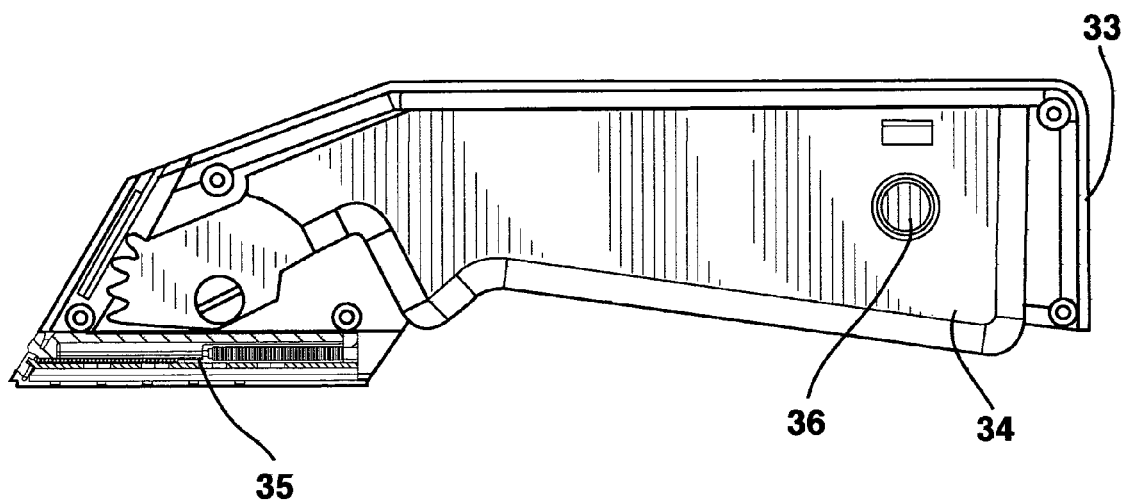
FIG. 8 is a side cutaway view of the surgical stapler assembly in the full closed position showing the components that comprise the removable staple cartridge assembly and the actuating trigger.
Figure 9:
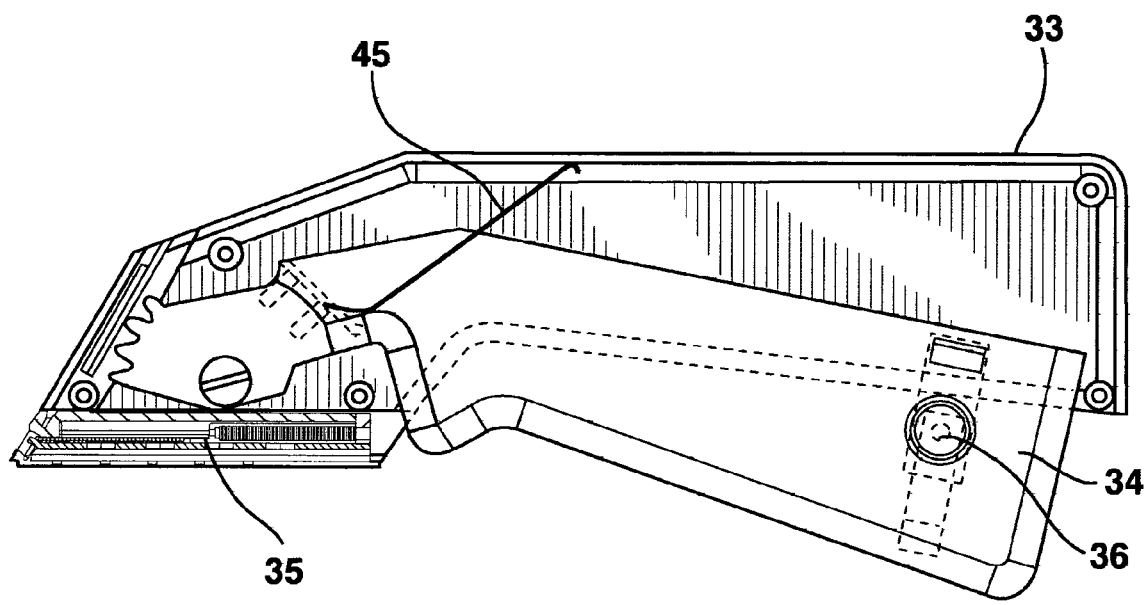
FIG. 9 is a cutaway side view of the stapler assembly showing the interaction of the actuating trigger and the return leaf spring.
Figure 10:
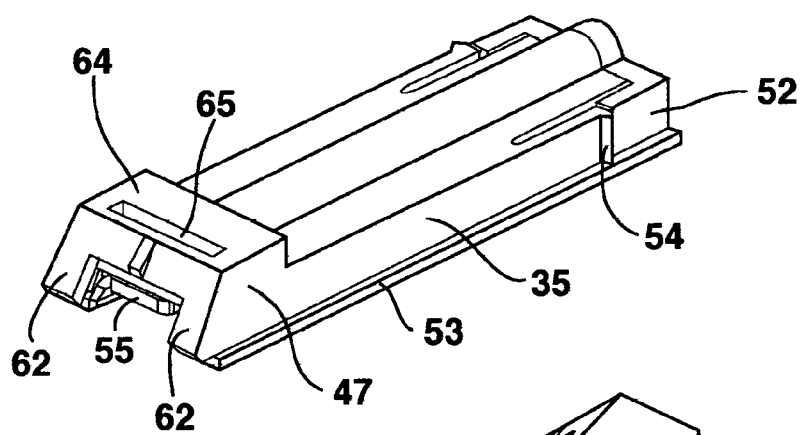
FIG. 10 a perspective view of the removable staple cartridge assembly showing all its comprising elements.
Figure 11:
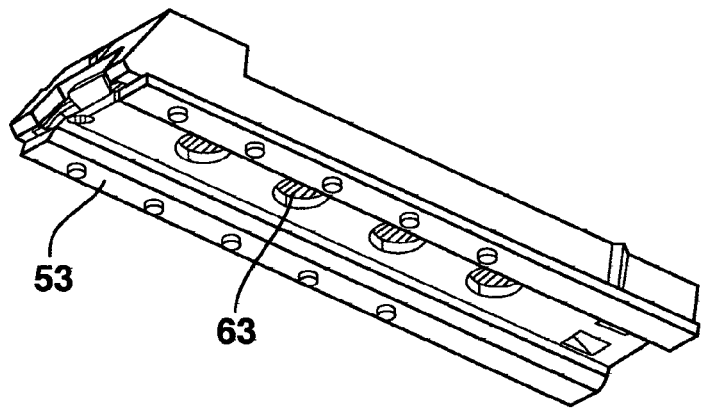
FIG. 11 a perspective view of the removable staple cartridge assembly showing the large holes for passive visual indication of the remaining staples.
Figure 12:
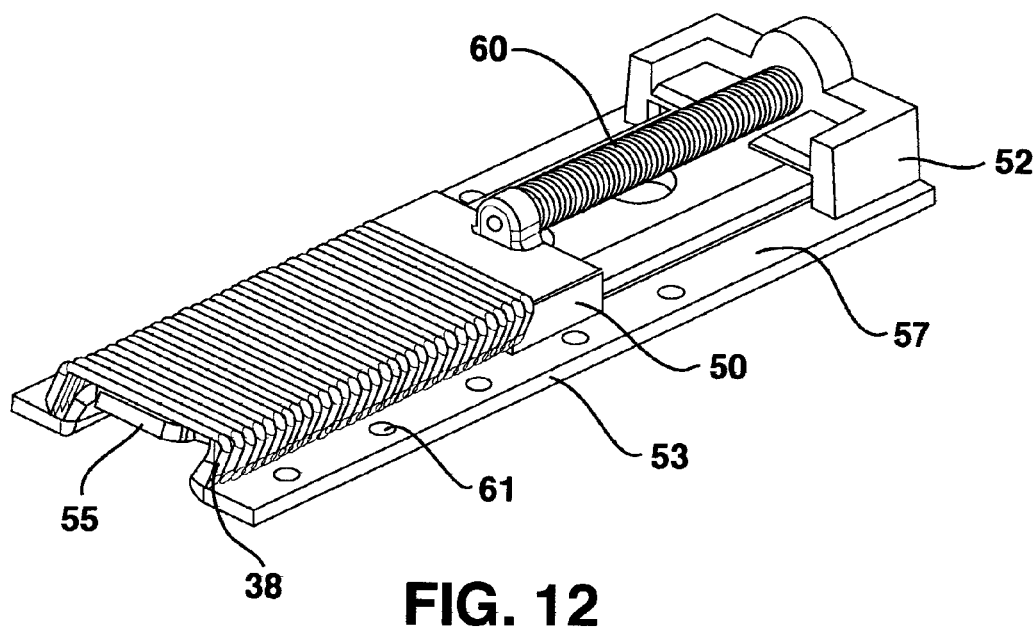
FIG. 12 is a perspective view of the removable staple cartridge assembly as shown in FIG. 7, but with the cartridge cover removed to reveal the inner components of the cartridge.
Figure 13:
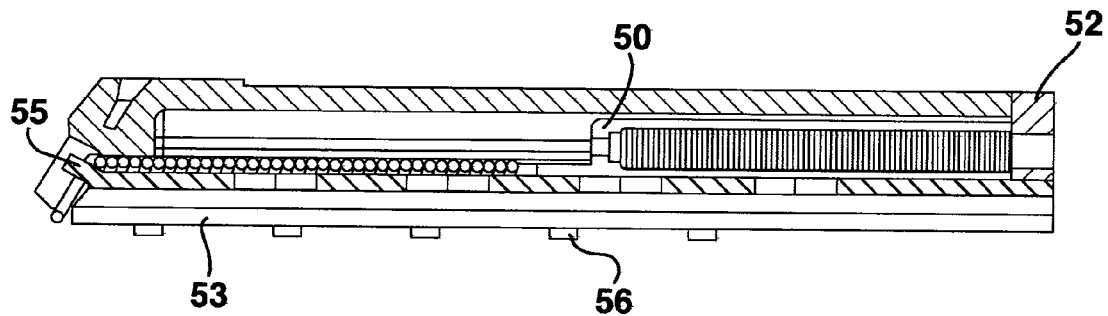
FIG. 13 is a section view of the removable staple cartridge assembly through a longitudinal plane showing all its components.
Figure 14:
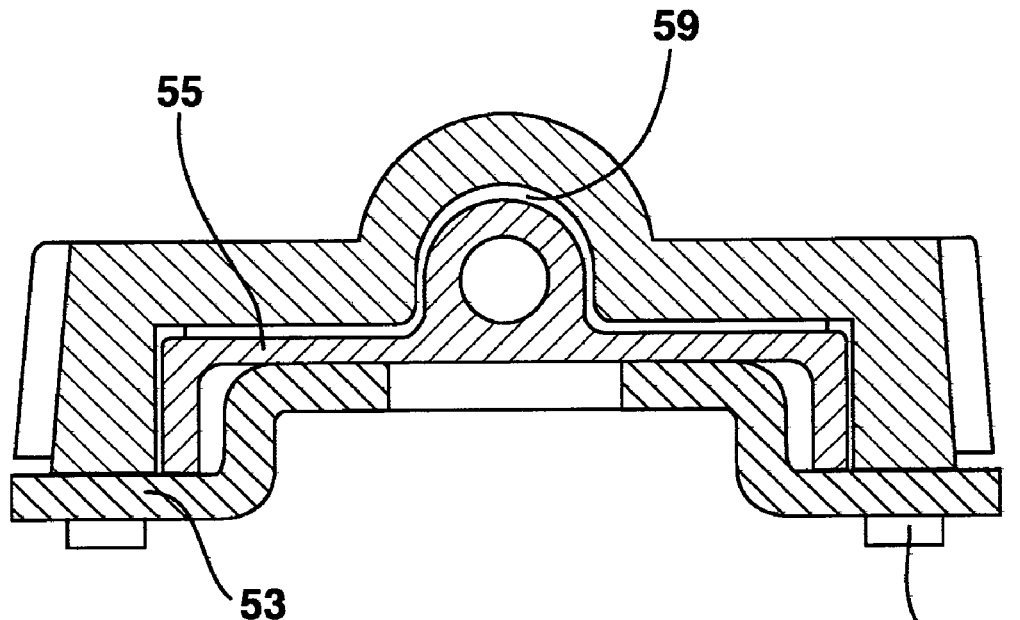
FIG. 14 is a cross section across the width of the removable cartridge assembly showing the location of the pusher in relation to the rest of the assembly.

FIG. 2 shows the stapler assembly 32 with the actuating trigger 34 in its full open position with respect to handle assembly 33 and a removable staple cartridge 35 ejected from the stapler. The handle assembly 33 and actuating trigger 34 are connected by a pivot screw 37, which allows trigger 34 to rotate about the center of the screw. Attached to the back end of the actuating trigger 34, there is a release mechanism 36. This release mechanism allows the engagement and disengagement of trigger 34 to handle 33. Trigger 34 is designed to operate in three main positions, fully open (FIG. 2), ready-to-use position (FIG. 1) and fully closed (FIG. 3). When trigger 34 is pulled to the fully open position a removable staple cartridge 35 is disengaged from forming tool 46 and can be removed and replaced by a new one. The detailed description of how this operation takes place will be described in detailed in later paragraphs. When stapler assembly 32 is in the ready-to-use position (FIG. 1). The snap feature 42 is engaged on lip 44 located in the inside wall of the stapler handle 33 as shown (FIG. 5). The snap features located in the release mechanism 42 prevent trigger 34 from fully opening during the normal operation of the devise. When the release buttons 43 are pressed the snap feature 42 clears the housing lip 44 allowing trigger 34 to fully open therefore permitting the discharge of the empty cartridge 36. FIG. 6 shows in detail the various components that form the release mechanism 36. The assembly is composed of a leaf spring 40 and two latches 41. Latches 41 are made out of a resilient plastic material, which can be heat staked or ultrasonic welded to the leaf spring 40. During the closing motion of the trigger 34, the snap features 42 in the latches 41 are forced against the inside surface of stapler handle 33. The spring action of leaf spring 40 allows the insertion of snap features 42 into the retention lip 44. While the dosing motion of trigger 34 is in no way restricted by the contact of snap features 42 against the inside wall of handle 33 it is obvious that the motion in the opposite direction would be prevented by the retention lip 44 (FIG. 7). Full closure of trigger 34 is reached when, as shown in (FIG. 8), the top surface of trigger 34 hits the inside top of handle 33. The return movement of the trigger 34 to the ready-to-use position is activated by the extension of leaf spring 45 as shown in (FIG. 9).

Figure 15:
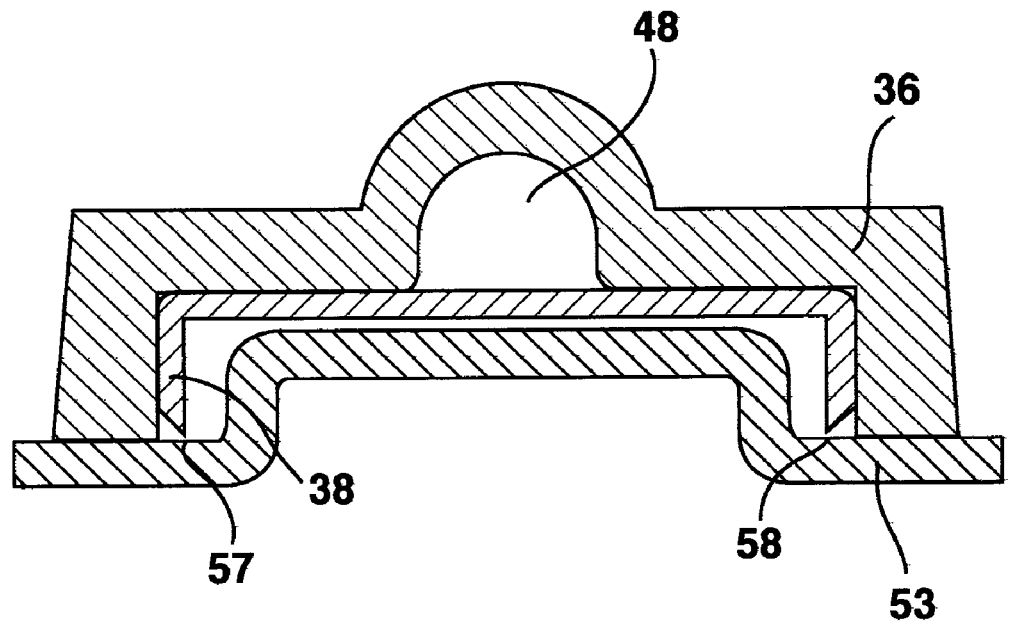
FIG. 15 is a cross section view of the removable staple cartridge assembly through the centerline of the staple body. This shows the position of the staple at an angle inside the cartridge assembly.
Figure 18:
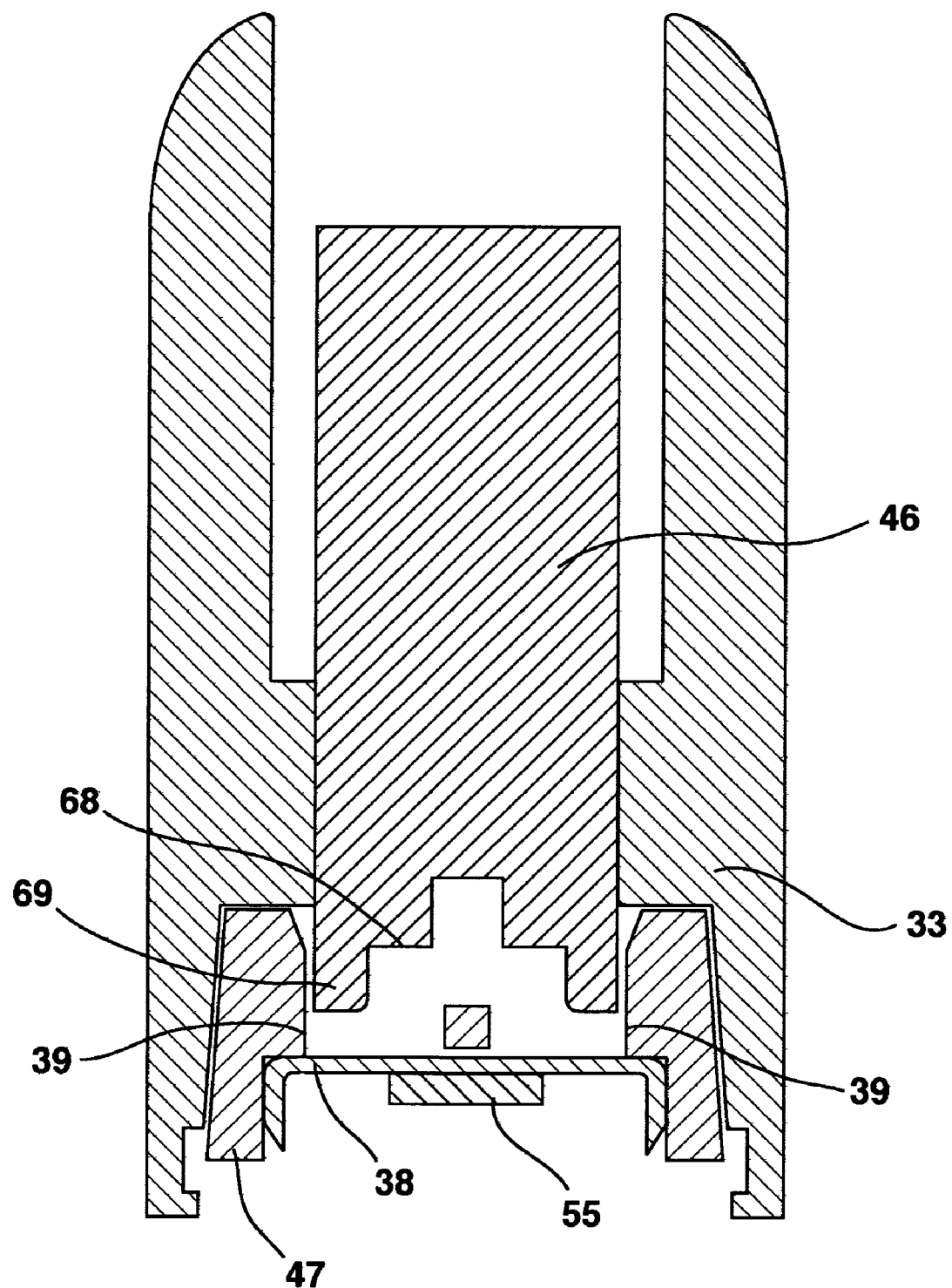
FIG. 18 is a section view through the width of the surgical stapler assembly in the ready-to-use position and across the forming tool showing the relative location of the forming tool with respect to the staple in the removable staple cartridge assembly.
Figure 19:
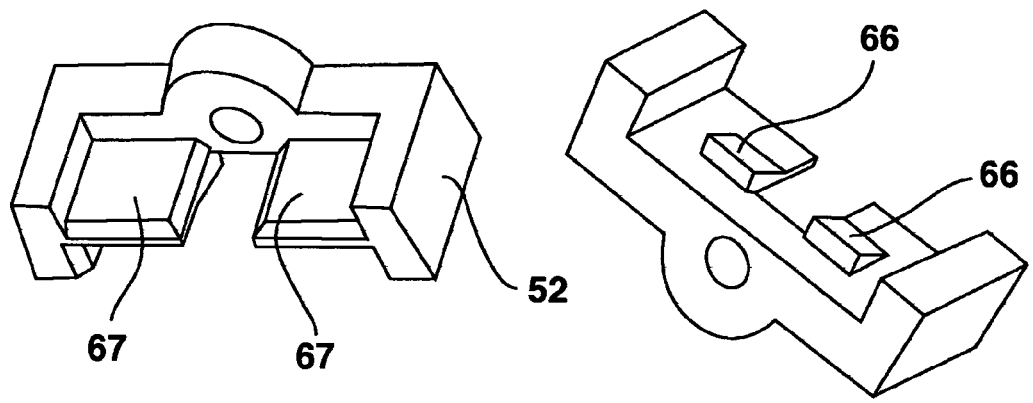
FIG. 19 is a perspective view of the removable staple cartridge assembly end cap.

FIGS. 10, 11, 12, and 13 show in detail the various components of the removable staple cartridge assembly 36. Removable staple cartridge assembly 35 includes a cartridge housing 47, an end cap 52, a rail 53, staples 38, a pusher 50, and a coil spring 60. The rail 53 consists of a high strength steel plate formed to provide the necessary surfaces for the staples 38 to ride on. At the front of rail 53 there is a formed tip or anvil 55 that provides support to the staple 38 during the its forming operation. In addition, rail 53 has 4 large holes 63 (FIG. 11) that provide the user with a visual indication of the number of staples 38 remaining in the removable staple cartridge 35. The cartridge housing 47 is made out of a resilient plastic material and is assembled to rail 63 by heat staking or ultrasonic welding the cartridge pins 56 to the holes 61 located on the side surfaces of rail 53. At the back end of the cartridge housing 47 there is a pair of cantilever snaps 54 that provide the means of engagement to the stapler handle 33 when the removable staple cartridge 35 is loaded into the stapler assembly 32. At the front end of cartridge housing 47 there is a tower 84 with an opening 65 (FIG. 10) that provides access to forming tool 45 once trigger 34 is rotated to the ready-to-use position and forces forming tool 46 into the window 65. As it will be explained in detail in the following paragraphs, this interaction is a very important since it is what allows the perfect alignment between forming tool 48 and a staple 38 just before being formed. Once the cartridge housing 47 and rail 53 are assembled they formed a cavity where a quantity of thirty-eight staples 38 are loaded (FIGS. 12, 13, 14, 15). When all the staples 38 are loaded they lay between rail 53 and the cartridge housing 47 at such an angle that when the stapler assembly 32 is in use the tips of staples 38 face perpendicular to the incision to be closed. FIG. 15 shows a cross section through removable staple cartridge 35 and through the centerline of staple 38. As shown, staple 38 is constrained by the inside walls of cartridge housing 47 and the tips ride on the surfaces 57 and 68 of rail 53. Pusher 60 provides a constant force against staples 38 via the compression force exerted by coil spring 60. Spring 60 is retained inside a cylindrical cavity 50 inside the cartridge housing 47. This allows spring 60 to extend only in the longitudinal direction of the removable staple cartridge 35. Once staple 38 is formed and pulled out of cartridge assembly 36 a new one is immediately located in placed by the force exerted by spring 60 and pusher 50. When the first staple 38 of the stack is in placed and ready to be formed, this one is retained at the front by two built In lips 62 into the cartridge housing 47 as shown in FIGS. 10, 11, 18 and 17). The mid-section of staple 38 is restrained by the anvil 55 and its side legs by the inside surfaces of cartridge housing 47 (FIG. 18). The end cap 52 is also made out of plastic and is assembled to the rail via two snaps 66 located at the bottom of end cap 52. The end cap surfaces 67 shown in FIG. 19 slide under the bottom surface of cartridge housing 47.

Figure 16:
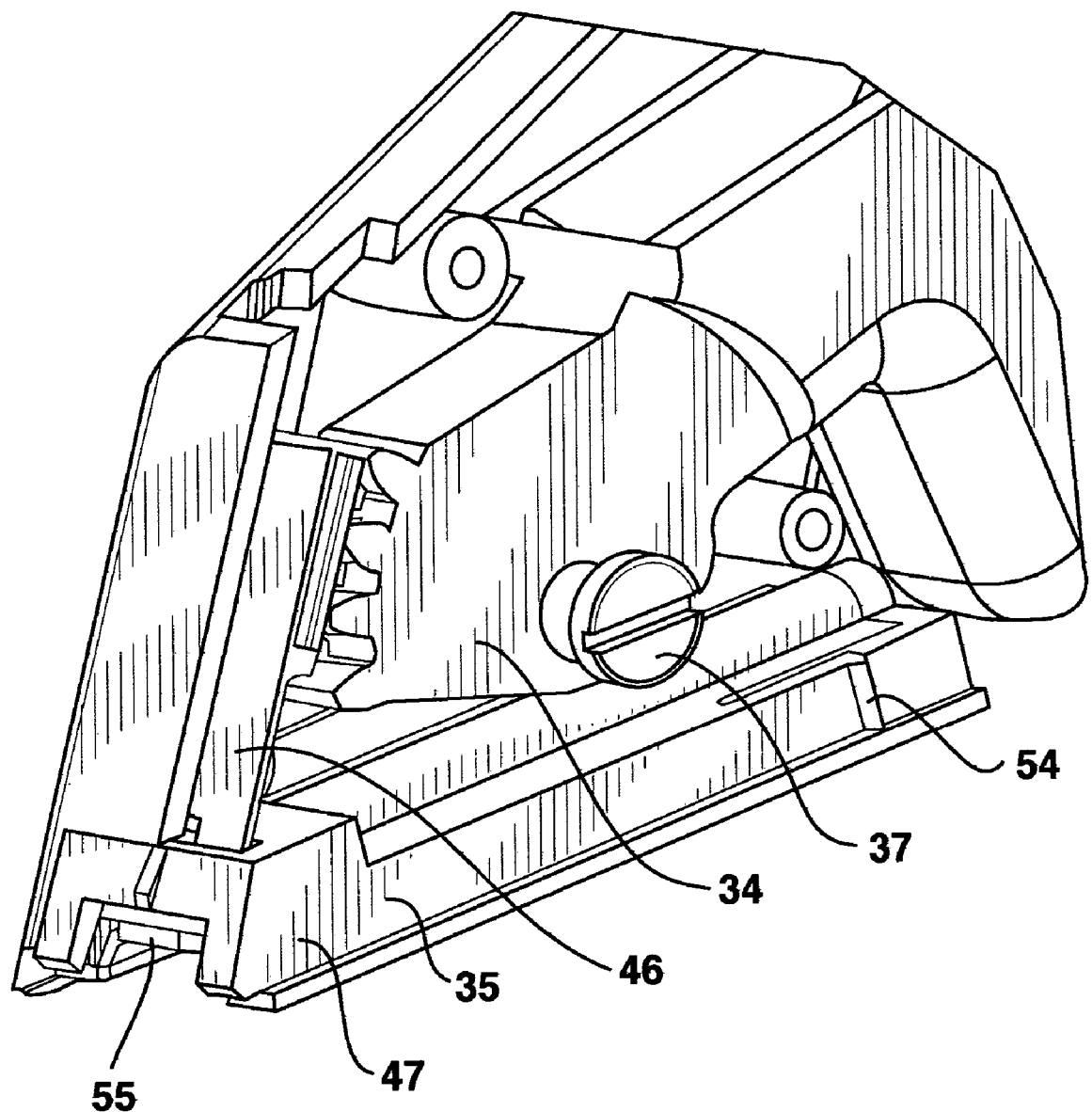
FIG. 16 is an enlarged cutaway perspective view of the surgical stapler assembly showing the interaction of the forming tool, actuating trigger and removable staple cartridge assembly in the ready-to-use position.
Figure 17:
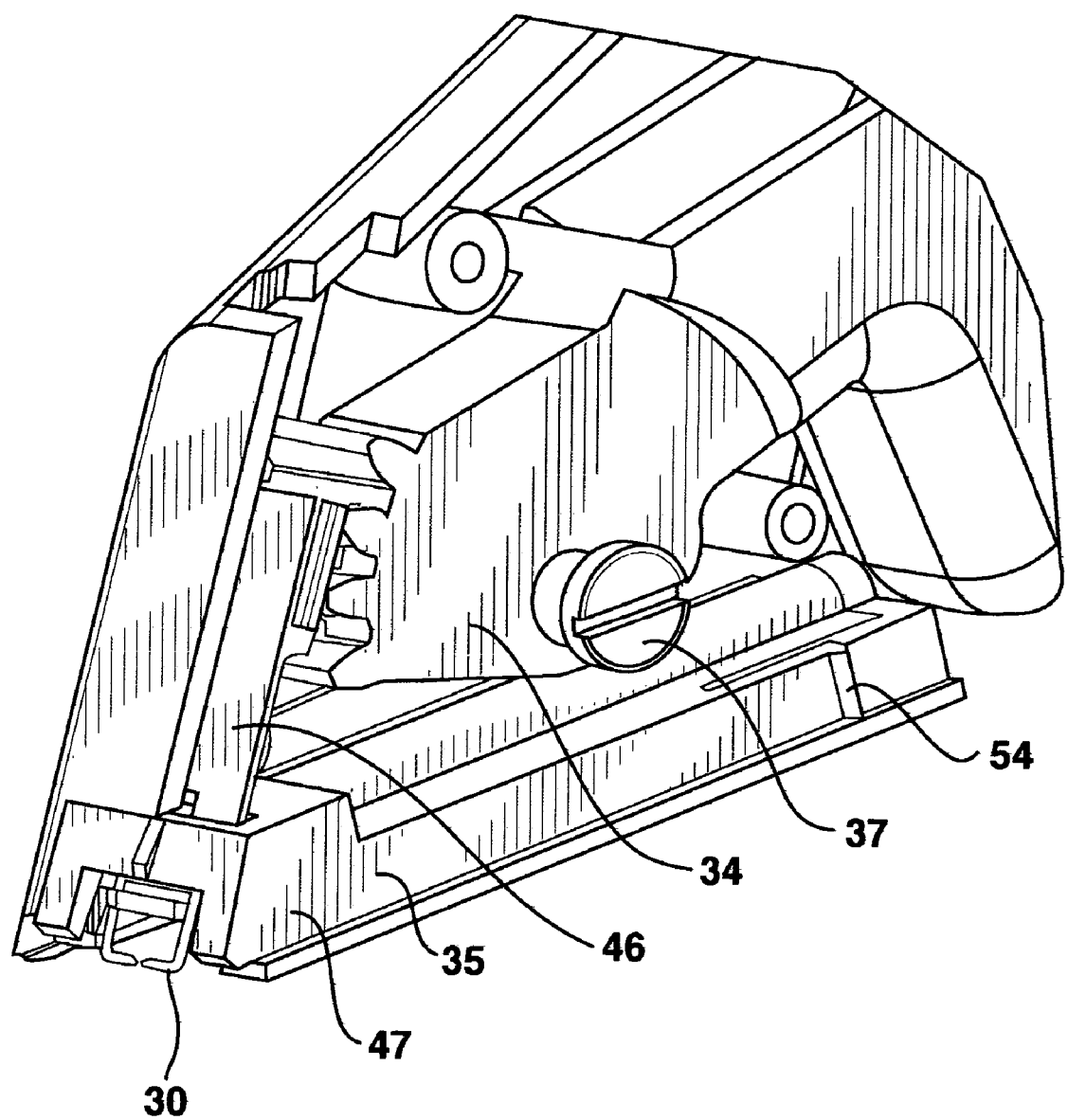
FIG. 17 is an enlarged cutaway perspective view of the surgical stapler assembly showing the interaction of the forming tool, actuating trigger and removable staple cartridge assembly in the full position with a surgical staple fully formed.
Figure 20:
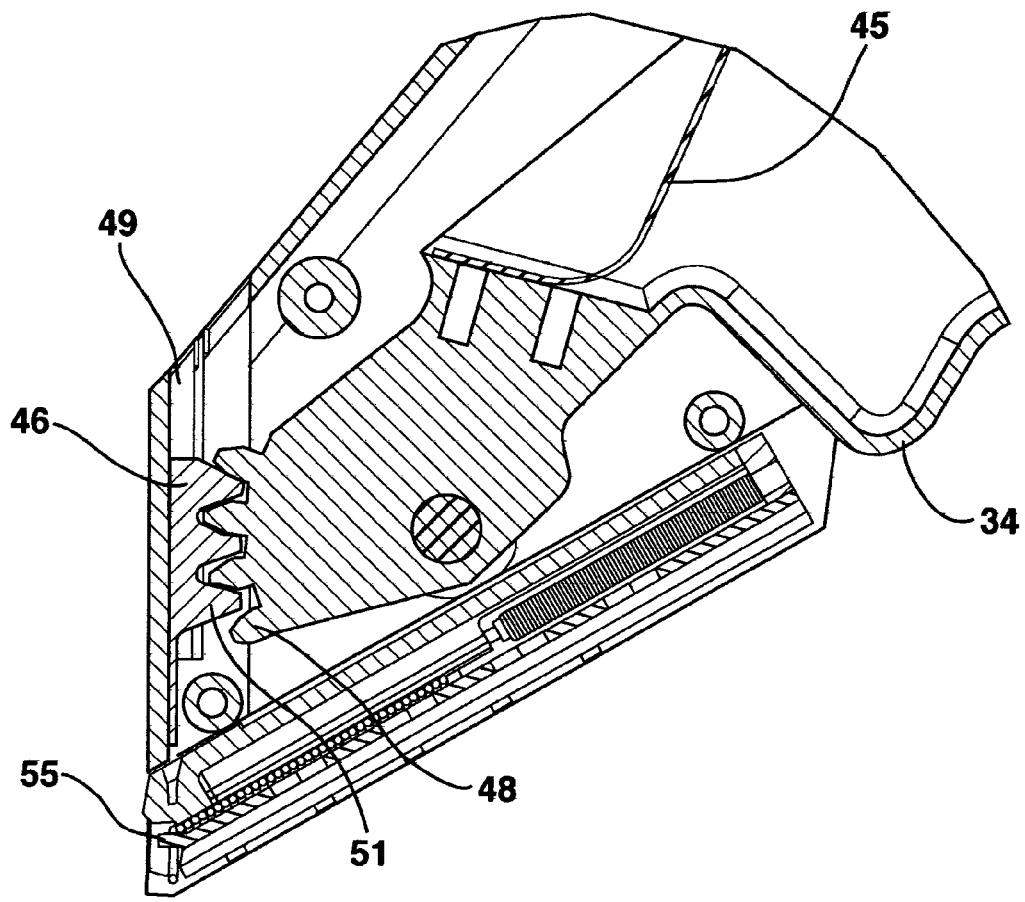
FIG. 20 is an enlarged longitudinal cross section view showing in detail the rack and pinion interaction among the gear teeth of the actuating trigger and the forming tool.
Figure 21:
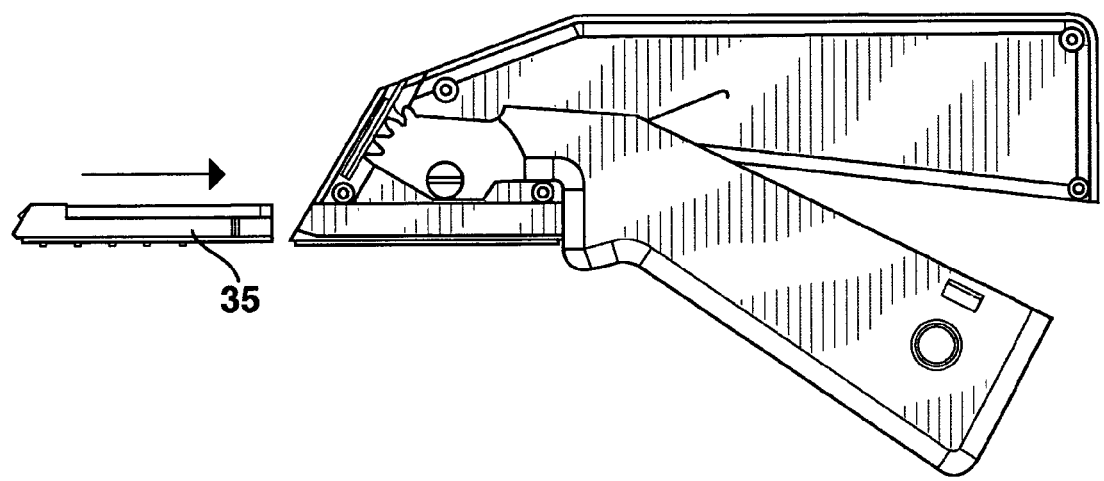
FIG. 21 is a cutaway view of the stapler assembly showing the actuating trigger in the fully open position and a removable staple cartridge being loaded.
Figure 22:
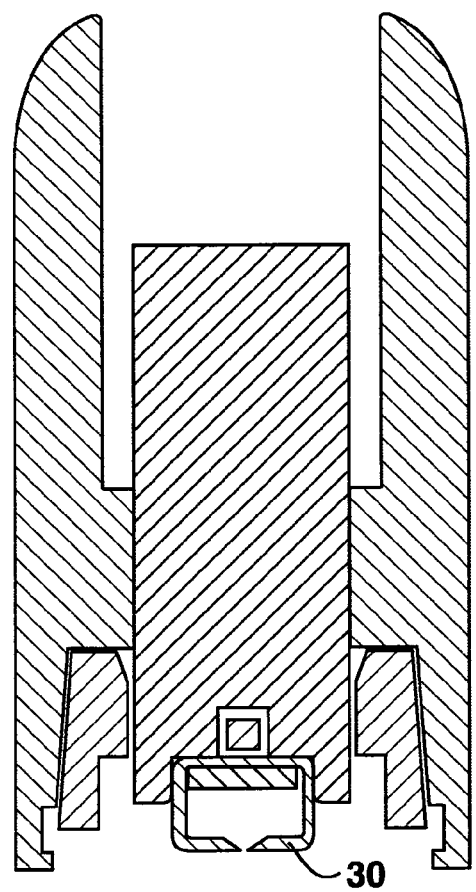
FIG. 22 is a section view through the width of the stapler assembly in the fully closed position and across the forming tool showing the relative location of the forming tool after a staple has been fully formed.

FIGS. 16, 18 and 20 show the relative positions of the components that form the staple feeding mechanism when the stapler 32 is in the ready-to-use position. In this arrangement, removable staple cartridge 35 is engaged in the handle 33 via the snaps 64 on removable staple cartridge housing 47. This prevents removable cartridge 35 from accidentally discharging from stapler assembly 32 when trigger 34 is in the fully open position. In addition, removable staple cartridge 35 is secured side to side by the walls of the stapler handle 33 (FIGS. 16, 18). The removable staple cartridge 35 is locked in position when forming tool 46 is pushed down during the rotation of trigger 34 to the ready-to-use position (FIGS. 9, 16, 18, 20). When a new removable staple cartridge 36 is inserted into the stapler handle 33 and trigger 34 is brought up from its fully open position (FIGS. 5, 21) to the ready-to-use position several actions take place. First, trigger 34 via its gear teeth 48 forces forming tool 46 to slide between the guides 49 inside the wells of stapler handle 33. Second, snap features 42 of release assembly 36 snap into the housing lip 44. Third, forming tool 46 engages into the window 65 (FIGS. 16, 20) of removable staple cartridge 35 and aligns and locks removable staple cartridge 35 into position (FIG. 18). At this point, forming tool 46 is completely aligned to the centerline of staple 38 and ready to be formed. This is very important to prevent jamming of the stapler during closing of the wound. The rack and pinion action between the teeth 48 of trigger 34 and the teeth 51 of forming tool 46 guarantees a very precise and smooth motion of the forming tool 46 inside the housing guides 49 of stapler housing 33 and window 65 of cartridge housing 36. When trigger 34 is actuated to the full closed position, its gear teeth 48 forces forming tool 46 downward to make contact with the top section of staple 38. At this point the extension logs 69 of forming tool 46 start the deformation of the staple legs. The mid section of staple 38 is resisted by anvil 56. This process continues until the edge 68 of forming tool 48 has completely reached bottom and presses against the top section of staple 26 (FIG. 15). When trigger 34 is In its full closed position and forming tool has completely finished its downward travel, the side legs of staple 38 then clear the lips 62 of cartridge housing 47 (FIGS. 3, 8, 17, 22) and staple 38 is free to clear removable staple cartridge 35 and being implanted into the wound. As soon as the staple 38 is out, the leaf spring 46 pushes trigger 34 back to the ready-to-use position and cartridge assembly pusher 50 and spring 66 push a new staple 38 into position. This process is repeated until all 38 staples 38 are utilized.

Although, the descriptions above contain many specificities, these should not be construed as limiting the scope of the invention, but merely providing illustrations. Thus, the scope of the invention should be determined by the appended claims and their legal equivalents, rather than by the examples given.

We claim:
1. A surgical stapler comprising:
a. a disposable staple cartridge, wherein said disposable staple cartridge having a staple feeding mechanism, wherein said staple feeding mechanism having a rail to guide staples contained within said disposable staple cartridge, and wherein said staple feeding mechanism having a window opening in a housing tower which engages a forming tool;
b. a handle assembly, wherein said handle assembly having a staple forming mechanism utilizing a forming tool to lock said disposable staple cartridge into said handle assembly, and wherein said handle assembly having a pivot screw to connect said handle assembly with an actuating trigger;
c. an actuating trigger, wherein said actuating trigger is pivotally connected in combination to said staple forming mechanism and said staple feeding mechanism secured in a frame, and wherein said actuating trigger is designed to operate in three main positions:
 (i) a fully opened position, wherein said disposable staple cartridge is disengaged from a forming tool and can be removed and replaced by a new one;
 (ii) a ready to use position, wherein gear teeth of said actuating trigger forces said forming tool to slide between guides inside walls of said handle assembly, wherein a rack and pinion action between said teeth of said actuating trigger and teeth of said forming tool guarantees a very precise and smooth motion of said forming tool inside said guides and said window opening in said housing tower of said disposable staple cartridge, wherein snap features of a trigger release assembly snap into a housing lip of said handle assembly, and wherein said forming tool engages into said window opening of said disposable staple cartridge and aligns and locks said disposable staple cartridge into position completely aligning said forming tool to a centerline of a staple ready to be formed preventing jamming of said staple during closing of a wound or incision;
 (iii) a fully closed position, wherein a top surface of said actuating trigger hits inside top of said handle assembly wherein said gear teeth of said actuating trigger forces said forming tool downward to make contact with a top section of a staple so that extension legs of said forming tool start the deformation of said legs, wherein a mid-section of said staple is resisted by an anvil continuing until an edge of said forming tool has completely reached bottom and presses against said top section of said staple, wherein said forming tool has completely finished a downward path of side legs of said staple, wherein said staple clears lips of said disposable staple cartridge, and wherein said staple is free to clear said disposable staple cartridge to be implanted in a wound or incision;
d. a trigger release mechanism, wherein said actuating trigger release mechanism having a leaf spring, wherein said actuating trigger release mechanism having two latches with two release buttons and two snap features, made out of a resilient plastic which are heat staked or ultrasonically welded to said leaf spring, wherein said trigger release mechanism allows engagement and disengagement of said actuating trigger with said handle housing, wherein pressing-in on said release buttons allows said snap features to disengage with a lip on said handle assembly housing allowing said actuating trigger to fully open permitting the discharge of an empty disposable cartridge, wherein said snap features when engaged with a lip on said handle assembly housing prevents said actuating trigger from fully opening in said ready to use position; and wherein said snap features during said closing motion do not restrict movement of said actuating trigger.
2. A surgical stapler comprising:
a. a disposable stapler cartridge, wherein said disposable staple cartridge is an assembly comprising:
 (i) staples;
 (ii) a rail, wherein said rail is a high strength steel plate formed to provide a surface for said staples to ride on;
 (iii) an anvil formed at the front of said rail to provide support to said staple during a forming operation;
 (4i) large holes on bottom surface of said raid to provide user a passive visual indication of the number of staples in said disposable staple cartridge;

(5i) a cartridge housing made out of a resilient plastic material assembled to said rail by heat staking or ultrasonically welding cartridge pins to holes located on both side surfaces of said rail;

(6i) a coil spring retained inside a cylindrical cavity of said cartridge housing allowing said coil spring to extend only in a longitudinal direction of said disposable cartridge assembly;

(7i) two lips built-in said cartridge housing for retaining said staple at the front in place and ready to be formed;

(8i) an end cap made out of resilient plastic material and assembled to said rail via two snaps located at the bottom of said cap, wherein said end cap surfaces slide under the bottom surface of said cartridge housing;

(9i) a pusher to provide a constant force against said staples via a Compression force exerted by said coil spring;

(10i) two cantilever snaps at the back end of said cartridge housing providing a means of engagement to said handle housing when said disposable staple cartridge is loaded into said surgical stapler;

(11i) a tower at the front end of said cartridge housing with a window opening that provides access to a forming mechanism once an actuating trigger is rotated to a ready-to-use position, and wherein said forming mechanism is in perfect alignment with said staple;

b. a handle assembly with a pivot screw;

c. an actuating trigger, wherein said actuating trigger is operable in three distinct positions;

d. a trigger release mechanism.

* * * * *